(12) United States Patent
Lekach et al.

(10) Patent No.: US 12,257,372 B2
(45) Date of Patent: Mar. 25, 2025

(54) APPARATUS AND METHOD FOR DIFFUSING A LIQUID COMPOSITION

(71) Applicants: Isaac Lekach, Beverly Hills, CA (US); Sam Ristich, Los Angeles, CA (US)

(72) Inventors: Isaac Lekach, Beverly Hills, CA (US); Sam Ristich, Los Angeles, CA (US)

(*) Notice: Subject to any disclaimer, the term of this patent is extended or adjusted under 35 U.S.C. 154(b) by 194 days.

(21) Appl. No.: 17/584,353

(22) Filed: Jan. 25, 2022

(65) Prior Publication Data

US 2023/0277711 A1  Sep. 7, 2023

(51) Int. Cl.
*A61L 9/03* (2006.01)

(52) U.S. Cl.
CPC .......... *A61L 9/037* (2013.01); *A61L 2209/111* (2013.01)

(58) Field of Classification Search
CPC ...... A61L 9/03; A61L 9/037; A61L 2209/111; A61L 2209/13; A61L 2209/135
See application file for complete search history.

(56) References Cited

U.S. PATENT DOCUMENTS 5,038,394 A * 8/1991 Hasegawa ........... A01M 1/2077
392/395

* cited by examiner

*Primary Examiner* — Lessanework Seifu
(74) *Attorney, Agent, or Firm* — Cotman IP Law Group

(57) ABSTRACT

Described is an apparatus, system, and methods, for the diffusing of a liquid composition that has an embedded receptacle. The supporting element for the embedded receptacle serves as the base for the apparatus may contain a light emitting diode that illuminates the components of the apparatus. The apparatus can handle various types of liquid compositions and could also be utilized to diffuse compositions containing oil, fragrances and/or cannabinoids such as cannabidiol or tetrahydrocannabinol.

20 Claims, 5 Drawing Sheets

APPARATUS AND METHOD FOR DIFFUSING A LIQUID COMPOSITION

BACKGROUND

Existing diffusers typically have a reservoir of water within which an oil is mixed. This water is then heated causing the oil and thereby the fragrance of the oil to be dispersed within a stream of steam that escapes from the reservoir. While effective this approach is messy and causes frequent water spillage when refilling the reservoir. The same amount of heat is applied regardless of the type of oil placed within the reservoir making these devices impractical or less effective in dispersing oils. These existing diffusers are also larger than desirable given that people typically use them in indoor or contained setting by placing the diffusers on countertops and in other such indoor locations.

To overcome these problems and limitations with the prior art there is a need for a system that can disperse fragrances without the use of a water reservoir, apply different heat durations and temperatures based on the type of liquid being dispersed and do so with a small form factor that is easily refillable.

SUMMARY OF THE INVENTION

One or more embodiments of the invention are directed to an apparatus for diffusing a liquid composition. This apparatus contains a supporting base that has a receptacle embedded within. To achieve a desirable look, the supporting element that serves as the base for the apparatus may contain a light emitting diode that illuminates the components of the apparatus.

The receptacle within the supporting base may be recessed into the supporting base and has a conductive element within that is connected to a power source. An insert containing an outer wall is configured to fit within the receptacle thereby coupling the insert with the receptacle. Both the insert and the receptacle may contain magnets to aid in coupling the two together. This insert may also contain a center receiving wall having one or more ventilation holes and a diffusing channel between the outer wall and the center receiving wall.

A vapor absorber fits within the diffusing channel and the ventilations holes permit diffusion of the liquid composition into a liquid absorber that fits with the center receiving wall. The insert also contains a heating coil configured to heat the liquid absorber and thereby vaporize the liquid composition being deposited on the liquid absorber when the liquid absorber reaches an appropriate temperature level.

A reservoir that serves as a chamber for holding the liquid composition can be coupled with or part of the insert. In one or more embodiments of the invention, the reservoir conveys liquid onto the liquid absorber when coupled with the center wall permitting the liquid composition to be dispensed onto the liquid absorber and thereby dispensing vapor out of the ventilation holes when the liquid composition is heated by the heating coil. The reservoir may be screwed into the insert's center wall using threading protrusions placed on the center wall or the reservoir may be coupled with the insert via any other acceptable manner. These threading protrusions on the center wall of the insert couple with a neck portion of the reservoir such that a user may couple the insert and the reservoir by screwing the neck of the reservoir into the center wall. When configured in this manner the insert serves as a bottle cap to the reservoir.

To provide power to the heating coil and/or other components within the insert, the receptacle contains a conductive element that when coupled with a receiving element within the insert provides power to the heating coil. This conductive element is a copper element or other suitable metal placed within the receptacle in one embodiment of the invention to enable power to be transfer to components within the insert that require power. The conductive element is arranged in a ring pattern at the base of the receptacle in one instance but can be placed anywhere it is able to contact with the receiving element on the insert. This conductive element is coupled to a power source and when the insert is connected to it transfers power to the receiving element on the insert and to other components within the insert such as the heating element.

The apparatus can handle various types of liquid compositions and may for example, be utilized to diffuse compositions contain oil, fragrances and/or cannabinoids such as cannabidiol or tetrahydrocannabinol.

One or more embodiments of the invention contain components that enable the apparatus to function with a degree of intelligence. For example, the apparatus may contain an identification chip that has information about the liquid composition and it may utilize this information to determine that heat setting for the heating coil are proper for the specific type of liquid composition in the reservoir. Any information that is helpful for properly diffusing the liquid composition may be encoded into the identification chip. For example, information such as composition type, batch information, and date of manufacture may be encoded into the identification chip. The proper heat settings for the liquid composition may also be contained with identification chip or obtained from a network-based data source in instances where the apparatus is able to access these data sources using networking components. To monitor the amount of the liquid composition dispensed by the apparatus a strain gauge may be utilized to monitor the dispensed amounts. In this example, the identification chip controls the amount of liquid composition dispensed by the apparatus. Other more specific components and functions will be described in further detail and illustrated in the accompanying drawings and detailed description which describe one or more embodiments of the invention.

DETAILED DESCRIPTION

Figure 1:
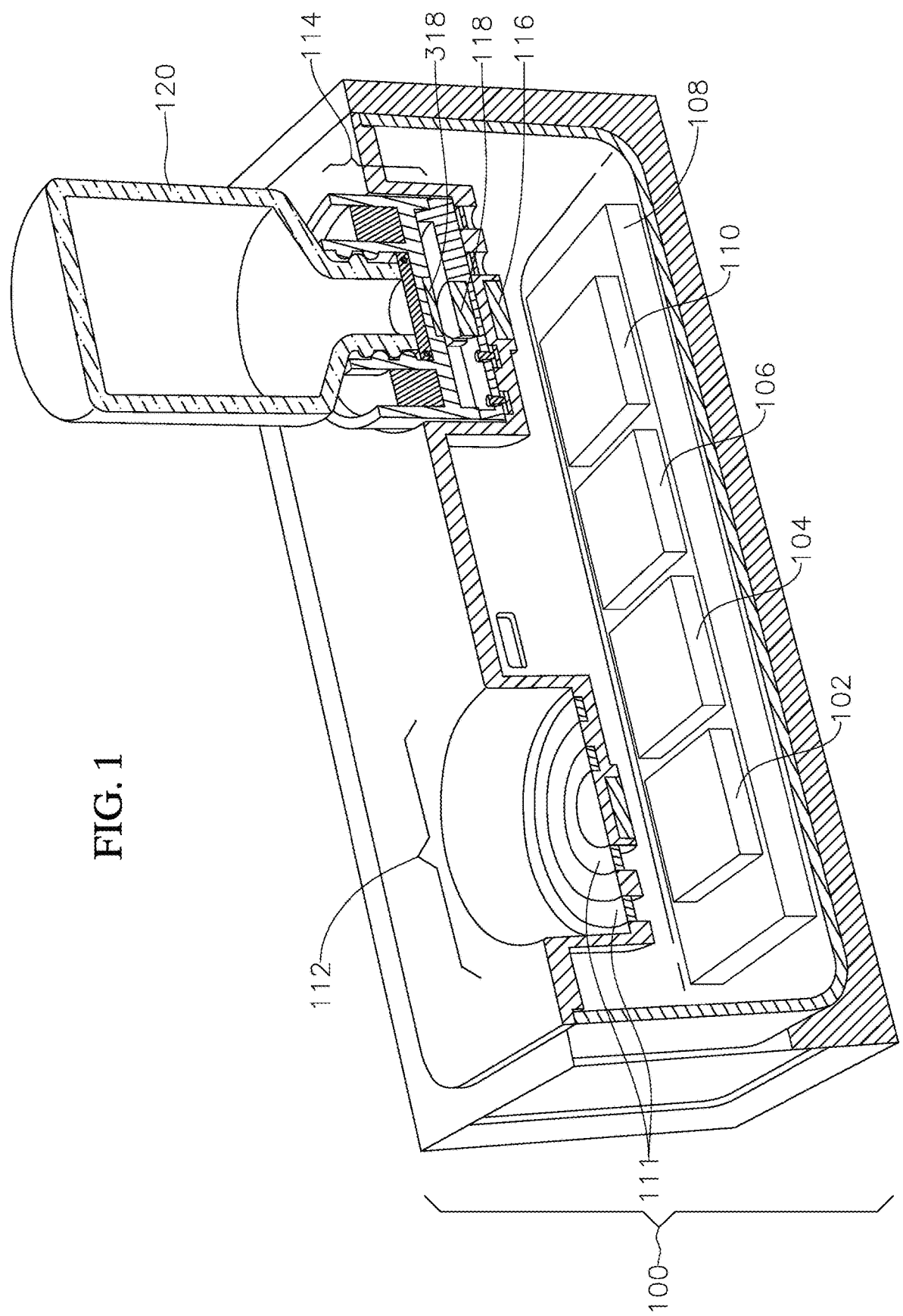
FIG. 1 illustrates a cross-sectional view of a supporting base with a recessed receptacle for an insert and reservoir holding a liquid composition configured in accordance with one or more embodiments of the invention.

An apparatus and method for diffusing a liquid composition will now be described in accordance with one or more embodiments of the invention.

In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. Furthermore, although steps or processes are set forth in an exemplary order to provide an understanding of one or more systems and methods, the exemplary order is not meant to be limiting. One of ordinary skill in the art would recognize that the steps or processes may be performed in a different order, and that one or more steps or processes may be performed simultaneously or in multiple process flows without departing from the spirit or the scope of the invention. In other instances, specific features, quantities, or measurements well known to those of ordinary skill in the art have not been described in detail so as not to obscure the invention. It should be noted that although examples of the invention are set forth herein, the claims, and the full scope of any equivalents, are what define the metes and bounds of the invention.

For a better understanding of the disclosed embodiment, its operating advantages, and the specified object attained by its uses, reference should be made to the accompanying drawings and descriptive matter in which there are illustrated exemplary disclosed embodiments. The disclosed embodiments are not intended to be limited to the specific forms set forth herein. It is understood that various omissions and substitutions of equivalents are contemplated as circumstances may suggest or render expedient, but these are intended to cover the application or implementation.

The term "first", "second" and the like, herein do not denote any order, quantity or importance, but rather are used to distinguish one element from another, and the terms "a" and "an" herein do not denote a limitation of quantity, but rather denote the presence of at least one of the referenced item.

Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

As used herein, the term "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

FIG. 1 illustrates a cross-sectional view of a supporting base with a recessed receptacle for an insert and reservoir holding a liquid composition configured in accordance with one or more embodiments of the invention. The supporting base (100) provides a housing for components such as a power source (102), networking components (104), and any needed microprocessors (106), circuit boards (108) and or memory (110) to interconnect and provide functionality and features to the apparatus. Depending upon which embodiment of the invention is implemented the functionality provided by the components within the supporting base (100) may not be needed or may be provided by an additional component such as a smart phone, watch or other computational device. A light emitting diode is optionally provided in one or more embodiments of the invention to illuminate the supporting base.

The power to the power source (102) can be provided utilizing battery power and/or through current provided from a wired power source. The receptacle (112) may transfer power to the insert (114) when the conductive element (111) on the receptacle (112) and the insert (114) make contact sufficient to enable the flow of electrical current. The receptacle (112) may, for example, contain copper elements arranged in a ring or other pattern at the bottom of the receptacle (112) or utilize other conductive elements positioned elsewhere on the receptacle (112). The insert (114) is coupled with or configured to contain a reservoir (120) for holding a liquid composition such as an oil, fragrance or other liquid intended for diffusion.

The supporting base (100) contains a receptacle (112) recessed into the supporting base (100). This receptacle (112) may take an array of different shapes and sizes and is depicted here as circular receptacle recessed into the supporting base (100). The shape and size of the receptacle however may vary in accordance with different embodiments of the invention. The key purpose of this receptacle (112) is to provide an element by which insert (114) may be coupled with the supporting base (100) and provided access to the power source (102). Thus, it is within the scope and spirit of this invention for any other coupling mechanisms to operate as receptacle (112). The receptacle (112) may also be a protrusion that couples with insert (114) if the shape of insert (114) is adopted to facilitate such an approach or receptacle (112) may take the form of a port, wire or other means to connect power to insert (114) to facilitate diffusion of a liquid composition.

The base of the receptacle (112) contains a first magnet (116) or other attachment mechanism that secures the insert (114) into position when the insert (114) is placed within the receptacle (112). In this embodiment of the invention, both the receptacle (112) contains a first magnet (116) and the insert (114) contains a first magnet (118). These magnets (116) and (118) are arranged with an attracting polarity to that insert (114) is held into place when placed in the receptacle (112).

Figure 2:
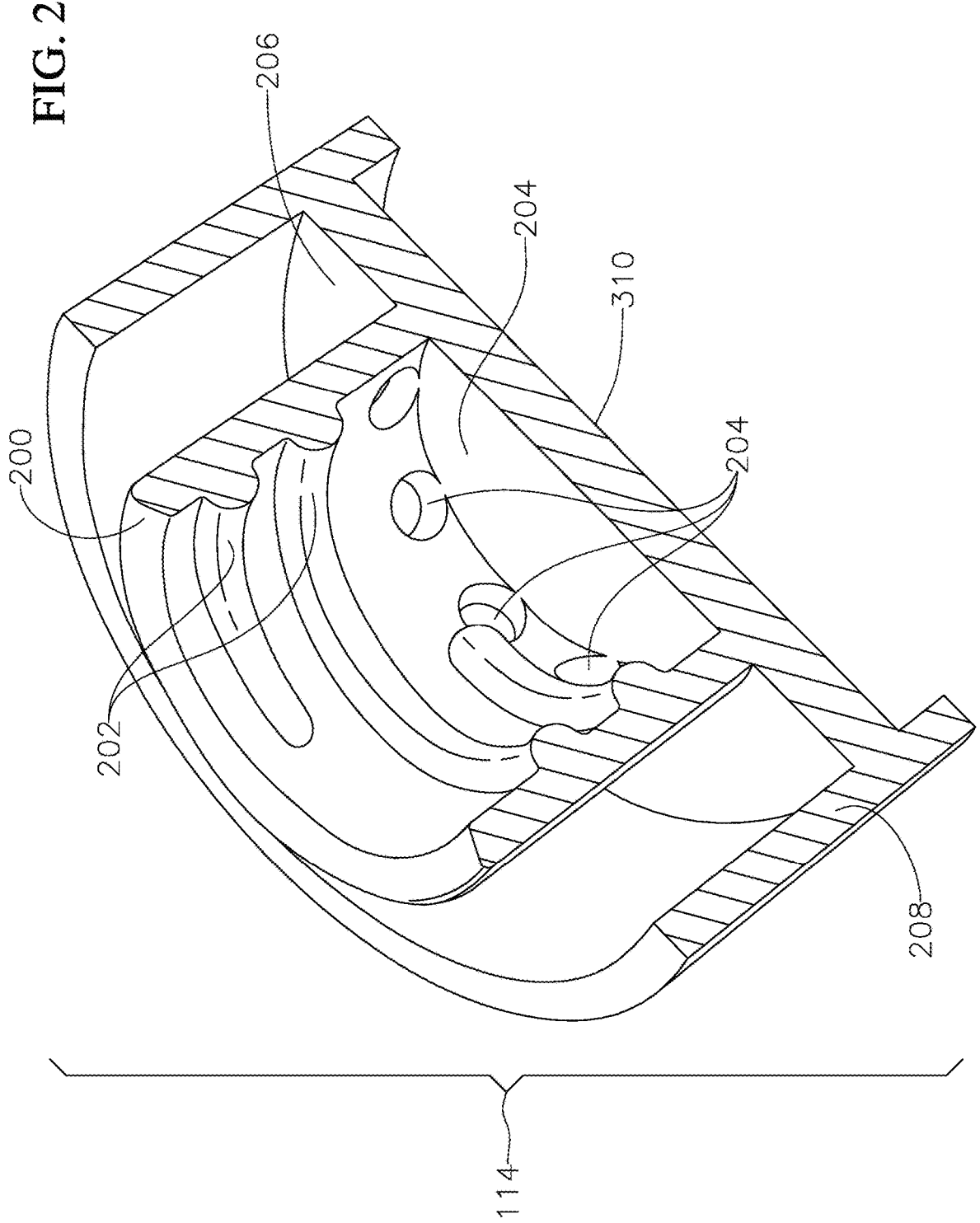
FIG. 2 illustrates a cross-sectional view of an insert configured in accordance with one more embodiments of the invention.

FIG. 2 illustrates a cross-sectional view of the insert (114) configured in accordance with one more embodiments of the invention. The insert (114) is configured to function as a type of bottle cap to the reservoir (120). To secure the insert (114) to the reservoir (120) the insert (114) has a center wall (200) having threading protrusions (202). These threading protrusions (202) serve as threading for attaching the neck of the reservoir (120) to the insert (114) although other attachment mechanisms are considered well within the scope and spirit of the invention. The threading depicted herein is just one example way to couple the reservoir (120) with the insert (114). The insert (114) may be fixedly attached to the reservoir (120) without a threading means or removably coupled with the reservoir (120) using the threading or another suitable approach. The base of the center wall (200) contains one or more ventilation holes (204). These ventilation holes (204) permit the liquid composition and/or vapors emanating from the liquid composition to flow into a diffusing channel (206). An outer wall (208) keeps any liquid or vapors within the diffusing channel (206) and serves as the element that fits the insert (114) within the receptacle (112).

Figure 3:
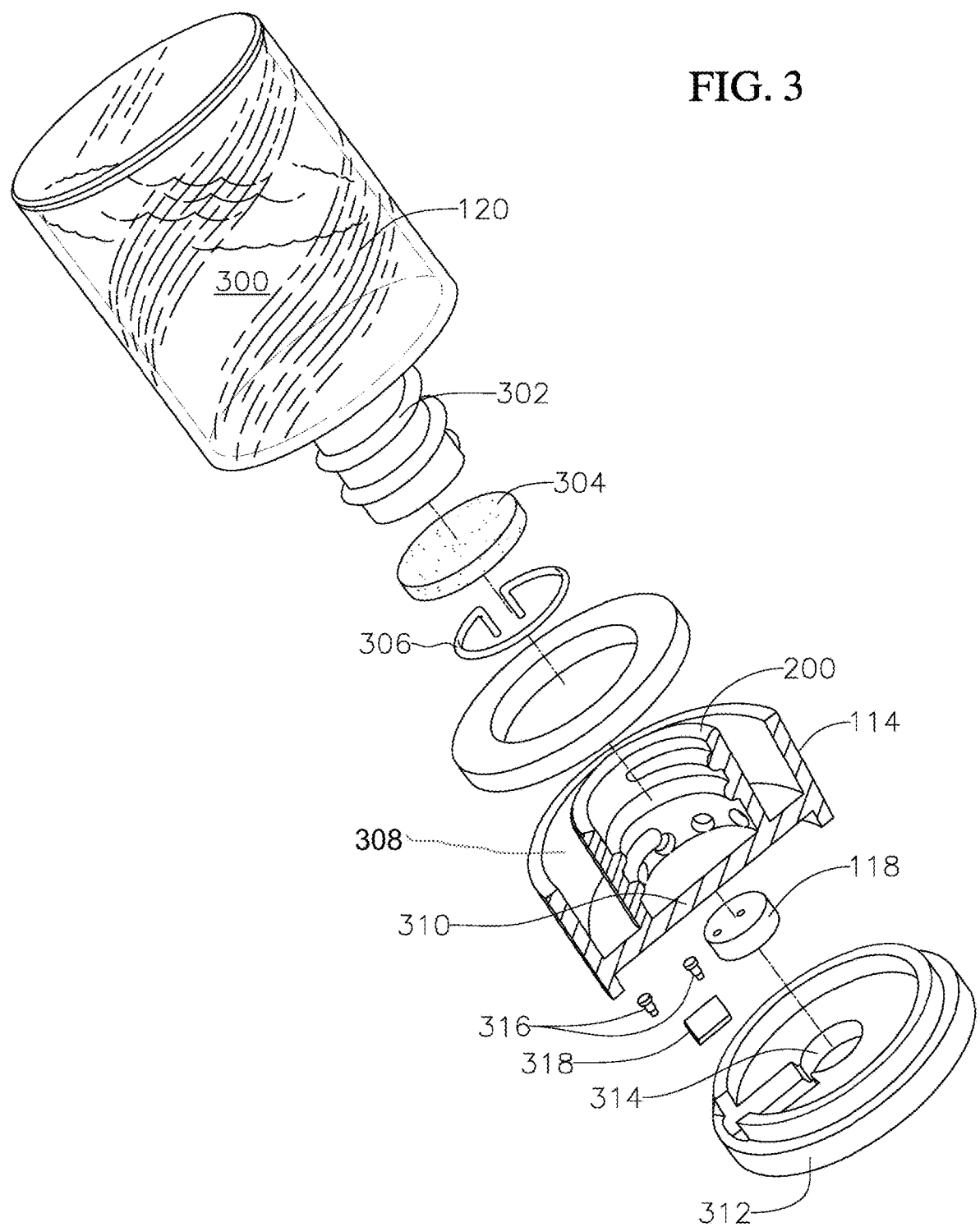
FIG. 3 illustrates an exploded view of the apparatus depicting the various components utilized to achieve a desired diffusion effect in accordance with one or more embodiments of the invention.
Figure 4A:
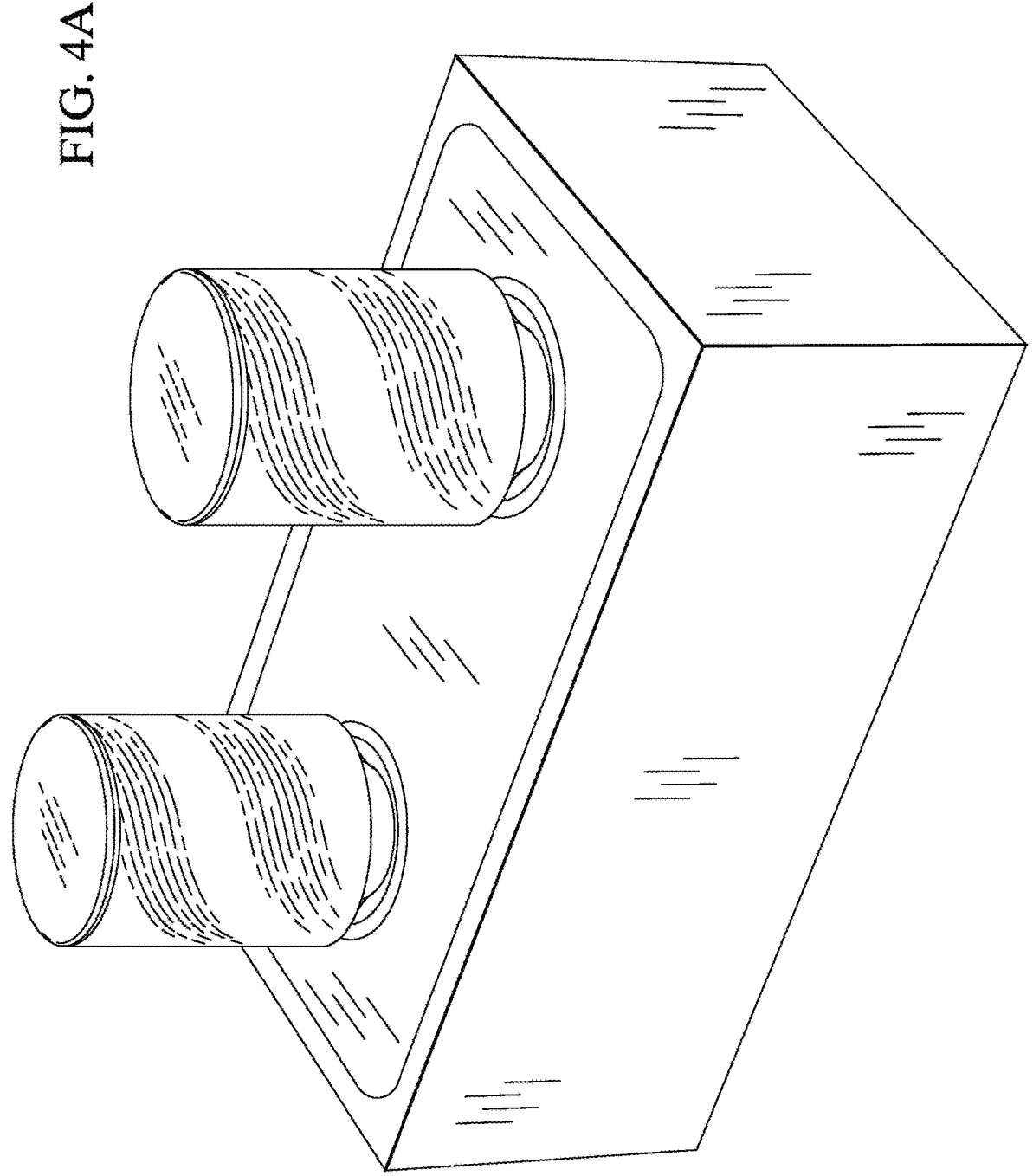
FIG. 4a-4d illustrate various perspective views of the design and appearance of one or more embodiments of the invention.
Figure 4B:
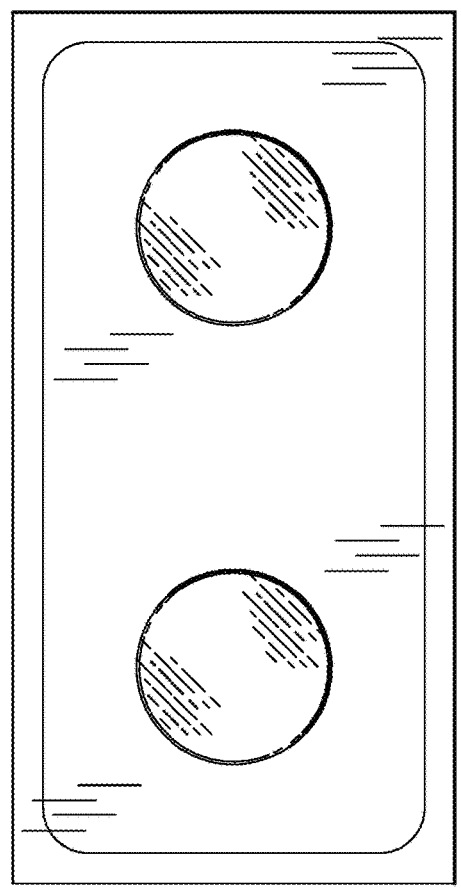
Figure 4C:
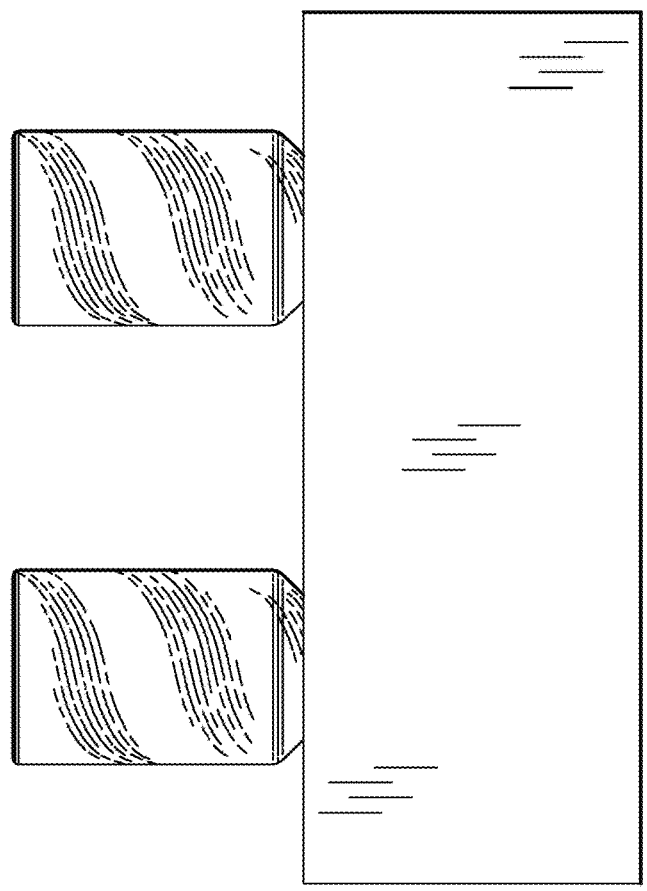
Figure 4D:
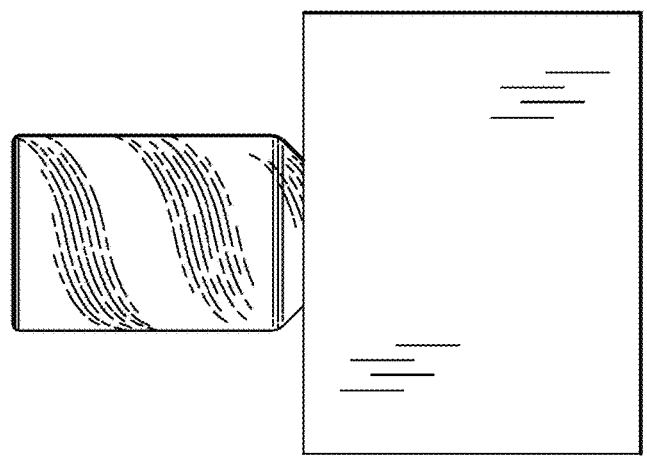

FIG. 3 illustrates an exploded view of the apparatus depicting the various components utilized to achieve a desired diffusion effect in accordance with one or more embodiments of the invention. The reservoir (120), provides a storage chamber for the liquid composition to be diffused. Liquid composition (300) is stored within this reservoir (120). The apparatus described herein is able to diffuse various liquid compositions and can, for example, diffuse compositions containing oil, fragrances, cannabinoids such as cannabidiol or tetrahydrocannabinol, and/or other compositions that are desirable to diffuse into a room, living space, vehicle or any other location where dispersal of the vapor from the liquid composition is desirable.

In one or more embodiments of the invention, the reservoir (120) has a neck portion (302) that contains neck threading enabling the reservoir (120) to be screwed into the insert (114) via the threading protrusions (202). In this embodiment the insert (114) acts as a sort of bottle cap for the reservoir (120). When the reservoir (120) is secured into the insert (114) with the neck portion (302) facing substantially downward, gravity enables the liquid composition (300) to flow onto a liquid absorber (304) that absorbs the liquid composition (300). This liquid absorber (304) is made of any material that is appropriately absorbent. Cotton, linen, rayon, bamboo fabric or any other material that can absorb liquid and not easily combust when heated to the degree required to vaporize liquid may be suitable. A heating coil (306) is configured to provide heat to the liquid absorber (304) and thereby heat the liquid composition (300) being absorbed into the liquid absorber (304). In one or more embodiments of the invention the heating coil (306) and the liquid absorber (304) fit within the center wall (200) of the insert (114). The center wall (200) has one or more ventilation holes (204) that permit vapors and/or liquid from the heated liquid composition (300) to flow into the vapor absorber (308) which resides, in one or more embodiments of the invention, within the diffuser channel (206) that sits between the center wall (200) and the outer wall (208). The heating coil (306) sits on a floor element (310) of the insert (114). This floor element (310) retains the liquid composition (300) within the insert (114) and prevents leakage of the liquid composition (300) into other parts of the insert (114). The center wall (200) and outer wall (208) extend from the floor element (310) thereby creating a well for the liquid compositions (300).

Below the floor element (310) a base element (312) provides a place for a magnet (118). This magnet (118) is integrated into or may be adjacent to the base element (312). In one or more embodiments of the invention, the magnet (118) fits within a recessed well (314) incorporated into the base element (312) although other alternative configurations are feasible and considered as being within the scope of the invention. The magnet (118) may, for example be flush mounted to the base element (312) rather than being held within the recessed well (314). The base element (312) also contains a conductive element (316) that functions to transfer electrical current obtain from the conductive element (111) and pass it to heating coil (306) to generate heat. Pogo pins or any other electrically conductive element may provide the functionality needed to pass electrical current to the heating coil (306). The base element (312) may take any shape that enables the functionality described herein but in one embodiment of the invention this base element (312) has an outer base wall that fits within the outer wall of the insert (114) thereby permitting the base element (312) to be coupled with the insert (114). The base element (312) may be removably coupled with or permanently coupled with or part of the insert (114) to form a connected unit. Similarly, the insert (114) may be removably or fixedly coupled with the reservoir (120) depending upon which embodiment of the invention is implemented.

A microprocessor (318) fits within the base element (312) or elsewhere in the insert (114). This microprocessor (318) serves in one or more embodiments of the invention as an identification chip able to relay information about the liquid composition (300) held within the reservoir (120). The chip may access information about the composition type, batch information and/or date of manufacture. The system may utilize this composition information to preferred heating parameters for the liquid composition (300) and the device may utilize this information to determine heat settings such as temperature range and duration for the heating coil (306). These heating parameters can be stored in memory within the device or chip itself or stored out in a network-based storage source such as the cloud so they may be updated from time-to-time as desired. When data to control the heating parameters resides in the cloud, networking components (104) provide a mechanism for accessing the data. Alternatively, the device may utilize the capabilities provided via a smartphone and simply link to the smartphone via Bluetooth or some other wireless interface to access the data needed to direct the heat levels of the device.

In one or more embodiments of the invention, a strain gauge or other measuring device is incorporated into the system to provide a way to monitor the amount of liquid composition (300) dispensed. The microprocessor may measure and/or control the amount of liquid dispensed.

FIG. 4a-4d illustrate various perspective views of the design and appearance of one or more embodiments of the invention.

Thus, one or more exemplary embodiments of an apparatus and method for diffusing a liquid composition has been described. The claims, however, when given their ordinary meaning to one of skill in the art and the full scope of all equivalents are what define the scope of the invention.

What is claimed is:

1. An apparatus for diffusing a liquid composition comprising:
   a supporting base having a receptacle embedded within, said receptacle having a conductive element connected to a power source;
   an insert comprising a floor element, an outer wall that extend up from said floor element and fits with said receptacle, a center receiving wall extending up from said floor element and having at least one ventilation hole, and a diffusing channel between said outer wall and said center receiving wall that utilizes said floor element;
   a vapor absorber that fits within said diffusing channel;
   a liquid absorber configured to fit within said center receiving wall;
   a heating coil configured to heat said liquid absorber and vaporize said liquid composition; and
   a reservoir for holding a liquid composition, wherein said reservoir is configured to convey said liquid composition to said liquid absorber when coupled with said center wall and said ventilation holes dispense vapor when said liquid absorber is heated by said heating coil.

2. The apparatus of claim 1 wherein said conductive element is within said receptacle.

3. The apparatus of claim 1 wherein said conductive element is a copper element configured to transfer current to said power source.

4. The apparatus of claim 3 wherein said copper element is arranged in a ring pattern within said receptacle.

5. The apparatus of claim 1 wherein said conductive element is a sending contact element configured to transfer current to a receiving contact element on said insert.

6. The apparatus of claim 1 wherein said insert contains a first magnet and said receptacle contains a second magnet that attracts said first magnet when said insert is placed within said receptacle.

7. The apparatus of claim 1 wherein threading protrusions are on said center wall of said insert and on a neck of said reservoir such that a user may couple said insert and said reservoir by screwing said insert onto said reservoir.

8. The apparatus of claim 1 wherein said insert serves as a bottle cap for said reservoir.

9. The apparatus of claim 1 wherein said liquid composition comprises an oil component.

10. The apparatus of claim 1 wherein said liquid composition has a fragrance.

11. The apparatus of claim 1 wherein said liquid composition comprises cannabinoids.

12. The apparatus of claim 1 wherein said supporting element contains a light emitting diode configured to illuminate said supporting element.

13. The apparatus of claim 1 further comprising:
   an identification chip comprising information about said liquid composition, wherein said information determines heat settings of said heating coil.

14. The apparatus of claim 13, wherein said information about said liquid composition comprises a composition type, batch information, and date of manufacture.

15. The apparatus of claim 14 wherein said heat settings are obtained from a network-based data source.

16. The apparatus of claim 13 further comprising:
   a strain gauge for monitoring an amount dispensed of said liquid composition.

17. The apparatus of claim 16 wherein said identification chip controls said amount dispensed of said liquid composition.

18. An apparatus for diffusing a liquid composition comprising:
   a supporting base having a receptacle embedded within, said receptacle having a conductive element therein which is connected to a power source;
   an insert comprising a floor element, an outer wall that extend up from said floor element and fits with said receptacle, a center receiving wall extending up from said floor element and having at least one ventilation hole, and a diffusing channel between said outer wall and said center receiving wall that utilizes said floor element;
   a vapor absorber that fits within said diffusing channel;
   a liquid absorber configured to fit within said center receiving wall;
   a heating coil configured to heat said liquid absorber and vaporize said liquid composition;
   a reservoir for holding a liquid composition, wherein said reservoir is configured to convey said liquid composition to said liquid absorber when coupled with said center wall and said ventilation holes dispense vapor when said liquid absorber is heated by said heating coil; and
   an identification chip comprising information about said liquid composition, wherein said information determines heat settings of said heating coil.

19. An apparatus for diffusing a liquid composition comprising:
   a supporting base having a receptacle embedded within, said receptacle having a conductive element connected to a power source;
   an insert comprising a floor element, an outer wall that extend up from said floor element and fits with said receptacle, a center receiving wall extending up from said floor element and having at least one ventilation hole, and a diffusing channel between said outer wall and said center receiving wall that utilizes said floor element;
   said insert having a first magnet and said receptacle having a second magnet that attracts said first magnet when said insert is placed within said receptacle;
   a vapor absorber that fits within said diffusing channel;
   a liquid absorber configured to fit within said center receiving wall;
   a heating coil configured to heat said liquid absorber and vaporize said liquid composition;
   a reservoir for holding a liquid composition, wherein said reservoir is configured to convey said liquid composition to said liquid absorber when coupled with said center wall and said ventilation holes dispense vapor when said liquid absorber is heated by said heating coil; and
   an identification chip comprising information about said liquid composition, wherein said information comprises a composition type and said information determines heat settings of said heating coil.

20. The apparatus of claim 19 wherein said heat settings are obtained from a network-based data source.

* * * * *